(12) United States Patent
Liao et al.

(10) Patent No.: US 10,808,025 B2
(45) Date of Patent: Oct. 20, 2020

(54) MONOCLONAL ANTIBODY INHIBITING IMMUNOSUPPRESSIVE FUNCTIONS OF PATHOGENS, ANTIGEN-BINDING FRAGMENT THEREOF, AND HYBRIDOMAS PRODUCING SUCH ANTIBODY

(71) Applicant: Sagabio Co., Ltd., Taipei (TW)

(72) Inventors: Kuang-Wen Liao, Hsinchu (TW); Yu-Ling Lin, Hsinchu (TW); Ting-Yan Jian, Hsinchu (TW)

(73) Assignee: SAGABIO CO., LTD., Taipei (TW)

( * ) Notice: Subject to any disclaimer, the term of this patent is extended or adjusted under 35 U.S.C. 154(b) by 0 days.

(21) Appl. No.: 16/577,549

(22) Filed: Sep. 20, 2019

(65) Prior Publication Data

US 2020/0010534 A1 Jan. 9, 2020

Related U.S. Application Data

(63) Continuation of application No. 15/165,723, filed on May 26, 2016, now Pat. No. 10,577,409.

(51) Int. Cl.
*C07K 16/12* (2006.01)
*A61P 31/04* (2006.01)
*A61K 39/00* (2006.01)

(52) U.S. Cl.
CPC ............ *C07K 16/121* (2013.01); *A61P 31/04* (2018.01); *A61K 2039/505* (2013.01); *C07K 2317/14* (2013.01); *C07K 2317/34* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 6,403,099 B1 | 6/2002 | Rappuoli et al. |
| 2004/0052799 A1 | 3/2004 | Smith et al. |

OTHER PUBLICATIONS

Skolnick et al. (Trends in Biotechnology 18: 34-39, 2000).
Greenspan et al. (Nature Biotechnology 7: 936-937, 1999).
Giusti et al. (Proc. Natl. Acad. Sci. USA. May 1987; 84 (9): 2926-2930).
Winkler et al (J. Imm., 265:4505-4514, 2000).
Chien et al. (Proc. Natl. Acad. Sci. USA. Jul. 1989; 86 (14): 5532-5536).
Caldas et al. (Mol. Immunol. May 2003; 39 (15): 941-952).
Casadevall et al. (PNAS vol. 109 No. 31, pp. 12272-12273).

*Primary Examiner* — Robert A Zeman
(74) *Attorney, Agent, or Firm* — Muncy, Geissler, Olds & Lowe, P.C.

(57) ABSTRACT

The present invention relates to a monoclonal antibody that inhibits immunosuppressive functions of pathogens, antigen-binding fragment thereof, and hybridomas producing such antibody. The monoclonal antibody or antigen-binding fragment thereof bind to a peptide consisting an amino acid sequence represented by MEKVGKDGVITVE (SEQ ID NO: 1). The present invention also discloses use of the invented monoclonal antibody or antigen-binding fragment thereof, and method of preparation for such hybridomas.

2 Claims, 9 Drawing Sheets

Specification includes a Sequence Listing.

PBS sera

Anti-HpHSP60 sera  LHp-1 (9E4)

LHp-2 (5A8)

PBS sera

Anti-HpHSP60 sera

LHp-1 (9E4)

LHp-2 (5A8)

LHp-1 (9E4)

MONOCLONAL ANTIBODY INHIBITING IMMUNOSUPPRESSIVE FUNCTIONS OF PATHOGENS, ANTIGEN-BINDING FRAGMENT THEREOF, AND HYBRIDOMAS PRODUCING SUCH ANTIBODY

CROSS REFERENCE TO RELATED APPLICATIONS

This application is a Continuation of co-pending application Ser. No. 15/165,723, filed on May 26, 2016, for which priority is claimed under 35 U.S.C. § 120; the entire contents of all of which are hereby incorporated by reference.

FIELD OF THE INVENTION

The present invention relates to a monoclonal antibody that inhibits the immunosuppressive functions of a pathogen, antigen-binding fragment thereof, and hybridomas producing such antibody, and especially to a monoclonal antibody that inhibits the immunosuppressive functions provided by an immunosuppressive substance secreted or produced by the pathogen, to enhance the immune system of host of the pathogen, and its antigen-binding fragment and hybridomas producing the antibody.

BACKGROUND OF THE INVENTION

Helicobacter pylori (H. pylori) is a Gram-negative bacterium that infects half of the adult population worldwide. The chronic inflammation triggered by H. pylori can lead to variable outcomes, such as peptic ulcers and gastric cancer, depending on the degree and extent of gastritis so caused. Although a predominant Th1-polarized mucosal immune response is activated in the host, the immune response is not sufficient to mount protective immunity against H. pylori, resulted in chronic infections and development of gastric pathologies in certain patient. Previous studies have revealed that H. pylori lysates can inhibit mitogen-induced T-cell proliferation, indicating that there are certain factors in the lysate relating to immunosuppressive activities. Such factors attenuate the T-cell activity, independent of the bacterial virulence genes CagA and VacA. Several mechanisms have been proposed to explain how H. pylori directly or indirectly suppresses T-cell-mediated immunity: H. pylori could inhibit T-cell proliferation and TCR expression by arginase, stimulate the release of the inhibitory cytokine TGF-β, interfere with invariant chain-dependent antigen presentation via VacA, negatively regulate the functions of DC via CagA phosphorylation, or suppress phagocytosis by professional phagocytes via VirB7 and VirB11.

Despite the possible involvement of the above-mentioned mechanisms, regulatory T-cells (Treg cells) are currently considered the main regulatory components in the inhibition of T-cell activity and in the balance of inflammation and bacterial persistence. In 2003, $CD4^+CD25^+$ T-cells were reported to be involved in H. pylori-induced immunopathology and colonization. Further investigations showed that host Treg cells are crucial in protecting an H. pylori-infected host against excessive gastric inflammation and disease syndromes, while at the same time promote bacterial colonization at the gastric and duodenal mucosa. Moreover, the expression of B7-H1 by gastric epithelial cells promotes the development of $CD4^+CD25^+FoxP3^+$ Treg cells following H. pylori exposure, which indicates that this pathogen promotes the induction of host Treg cells. Subsequent studies examined the functions of these H. pylori-induced Treg cells and showed that they can suppress the activity or induce the anergy of H. pylori-specific effector T cells. In addition, H. pylori-induced gastritis is associated with a recruitment of naturally occurring $FoxP3^+$ Treg cells that correlate with the degree of bacterial colonization and mucosal TGF-β1 expression. Collectively, these findings indicate that host Treg responses induced by H. pylori infection are important regulators of the immune response to H. pylori and are involved in the pathogenesis of H. pylori-related diseases.

H. pylori heat shock protein 60 (HpHSP60) can induce the expression of proinflammatory cytokines and TGF-β1 in monocytes. HpHSP60 has been reported to be expressed in the bacterial cell wall, associated with urease, and can function as an adhesive molecule for gastric epithelial cells. In addition, the administration of an anti-HSP60 antibody was found to interfere with the growth of H. pylori. Therefore, HpHSP60 is not only an essential factor for the viability of H. pylori but is also an important product that facilitates colonization of the human stomach. However, many studies have shown that HpHSP60 acts as a potent immunogen, leading to the strong induction of proinflammatory cytokines, such as TNF-α, IL-8, and IL-6. These cytokines determine inflammation at the site of infection, and such HpHSP60-induced inflammation might have the potential to promote processes of malignant tumorigenesis, including angiogenesis and metastasis. HpHSP60 is also an important virulence factor for H. pylori infection in a human host.

Taken together, the relationship between HpHSP60 and Treg cells is intriguing and deserves further investigations. However, most past researches focus on inflammation induced by HpHSP60. Very few researches talked about the relationship between HpHSP60 and the immunosuppressive reactions expressed in a host.

U.S. Pat. No. 6,403,099 disclosed conjugated compounds comprising a heat shock protein and capsular oligosaccharide or polysaccharide. The compounds are capable of inducing formation of anti-polysaccharide antibodies. The heat shock protein includes H. pylori heat shock protein.

SUMMARY OF THE INVENTION

According to this invention, certain pathogens are capable of suppressing the immunity of their hosts. Such immunosuppressive functions are especially provided by immunosuppressive substances secreted or produced by the pathogens. It is possible to block the immunosuppressive functions of the pathogens by shutting down functions of the immunosuppressive substances. Since the immunosuppressive functions have been shut down, the immunity activities of the host is not suppressed. The unsuppressed or increased immunity functions of the host are then capable of reducing or even eliminating the pathogens.

The inventors have found a novel monoclonal antibody that significantly inhibits the immunosuppressive functions or substances of particular pathogens. Based on this discovery, the monoclonal antibody of this invention, its antigen-binding fragment, hybridomas to produce such antibodies, as well as preparation methods thereof, are invented.

Accordingly, an objective of the invention is to provide a novel monoclonal antibody. The monoclonal antibody has significantly inhibits the immunosuppressive functions of particular pathogens.

Another objective of this is also to provide antigen-binding fragment of the monoclonal antibody, as well as hybridomas that generate such antibody.

Another objective of the present invention is to provide methods for preparation of the monoclonal antibody, its antigen-binding fragment and hybridomas that generate such antibody.

Another objective of the present invention is to provide uses of the monoclonal antibody, its antigen-binding fragment and hybridomas that generate such antibody.

According to one aspect for the present invention, the monoclonal antibody or antigen-binding fragment thereof are combinable to a peptide comprising an amino acid sequence represented by MEKVGKDGVITVE (SEQ ID NO 1).

The present invention also provides hybridomas capable of producing the monoclonal antibody or its antigen-binding fragment.

The monoclonal antibody of the invention expresses significant inhibitive effects against immunosuppressive activities of particular pathogens and is useful in blocking an immunosuppressive phenomenon caused by the pathogens. In certain embodiments of the present invention, the immunosuppressive function of pathogens is provided by an immunosuppressive substance secreted or produced by the pathogens. In such embodiments, the monoclonal antibody or its antigen-binding fragment of the present invention primarily eliminate the pathogens by inhibiting the immunosuppressive functions of the pathogens, and therefore activating immune responses of the host of the pathogens.

According to another aspect, the present invention provides methods for preparation of a monoclonal antibody or its antigen-binding fragment, and hybridomas capable of producing the antibody or the fragments, the method comprising: using a peptide comprising an amino acid sequence represented by MEKVGKDGVITVE (SEQ ID NO 1) as an antigen to cause a mammal to generates an immune response to the antigen; obtaining an immune cell from the mammal immunized against the pathogens and fusing the obtained immune cell with a mammalian myeloma cell to produce a hybridoma; cloning the obtained hybridoma to obtain a desired hybridoma. The method of the present invention may further comprise the steps of: using the obtained hybridoma to produce antibodies; and harvest the antibodies produced by the hybridoma.

In a preferred embodiment of the present invention, the immune cell includes a spleen cell.

The invented monoclonal antibody or its antigen-binding fragment can be used directly, or as a pharmaceutical composition that includes pharmaceutically acceptable additives etc. According to one embodiment of the present invention, a pharmaceutical composition is provided and comprises a monoclonal antibody, or antigen-binding fragment thereof, of the present invention. According to another embodiment of the present invention, the pharmaceutical composition is used as a functional inhibitor against particular immunosuppressive substances. Further, the present invention also provides use of the invented monoclonal antibody, including in the preparation of a pharmaceutical composition.

DETAILED DESCRIPTION OF THE INVENTION

Figure 1:
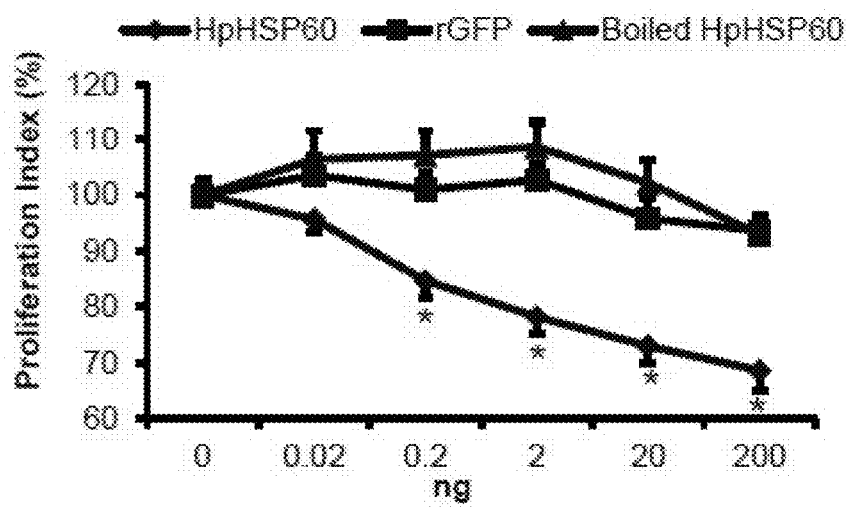
FIG. 1 shows experimental results on effects of HpHSP60 on PBMC proliferation.

Although it is not intended to limit the present by any theory, according to this invention, certain pathogens are capable of suppressing the immunity of their hosts, by secreting or producing immunosuppressive substances, so to proliferate or to cause disease to the host. Examples of such pathogens include *H. pylori* and other similar bacteria such as *Helicobacter* fells and *Arcobacter suis*. The inventors found that heat shock protein is one of such immunosuppressive substances. According to embodiments of this invention, *H. pylori* heat shock protein 60 (HpHSP60) is capable of reacting with monocytes to stimulate the production of immunosuppressive hormones, such as IL-10 and TGF-β, and induce the proliferation of Treg cells. As a result, the immunity of the host is suppressed, making the host unable to resist the chronic infections of *H. pylori*.

The present invention has developed a novel method to increase the immunity of hosts. A function inhibitor that blocks the functions of the immunosuppressive substances is used to shut down the functions of the immunosuppressive substances. Proliferation of Treg cells is thus effectively inhibited and immunosuppressive response of the host is eliminated.

The inventors have discovered a novel monoclonal antibody that significantly inhibits the immunosuppressive functions or substances of particular pathogens. The monoclonal antibody or its antigen-binding fragments may thus be used as the functional inhibitor that is capable of identifying the immunosuppressive substance or a fragment thereof and blocking functions of the immunosuppressive substance.

Deposit

The LHP-1 (9E4) antibody was generated by using the amino acid sequence of positions 101 to 200 of HpHSP60 as antigen. Hybridomas including this antibody, LHP-1 (9E4), were deposited with the American Type Culture Collection (ATCC®), 10801 University Boulevard, Manassas, Va., 20110, USA, ATCC Accession Number PTA-122900. The date of deposit is Mar. 2, 2016.

Monoclonal Antibodies and Hybridomas

The monoclonal antibody or its antigen-binding fragment of the present invention binds to a peptide comprising an amino acid sequence represented by MEKVGKDGVITVE (SEQ ID NO 1) and are capable of effectively inhibiting immunosuppressive reactions induced by particular pathogens. The immunosuppressive functions of the pathogens are provided by an immunosuppressive substance secreted or produced by the pathogens. The monoclonal antibody or its antigen-binding fragment of the present invention primarily eliminates the pathogens by inhibiting the immunosuppressive functions of the pathogens, and therefore activating immune responses of the host of the pathogens. The invented monoclonal antibody or its antigen-binding fragment expresses significant functional inhibition activities against the immunosuppressive functions induced by the pathogens, with unexpected effects.

According to one embodiment of the present invention, the antibody or its antigen-binding fragment recognizes a peptide comprising an amino acid sequence represented by MEKVGKDGVITVE (SEQ ID NO 1).

The antibody or its antigen-binding fragment of the present invention may contain a heavy chain and/or light chain. Each light chain and heavy chain may include a variable region at their N-terminals and alternating zones including 4 framework regions (FR) and 3 complementary determining regions (CDR) in each of the variable regions.

In one embodiment of the invention, the antibody or its antigen-binding fragment may include in a variable region of the light chain: CDR1 comprising an amino acid sequence represented by ASQSVDYDGDVFL (SEQ ID NO 2) CDR2 comprising an amino acid sequence represented by YAASN (SEQ ID NO 3), and CDR3 comprising an amino acid sequence represented by QSNEVPWT (SEQ ID NO 4). In a preferred embodiment, a variable region of the light chain comprises an amino acid sequence represented by SEQ ID NO 5, i.e., positions 21-131 of SEQ ID NO 6.

In some embodiments of the invention, the antibody or its antigen-binding fragment comprises at a variable region of the heavy chain: CDR1 comprising an amino acid sequence represented by SGFTFSSFG (SEQ ID NO 7), CDR2 comprising an amino acid sequence represented by ISNGGS (SEQ ID NO 8), and CDR3 comprising an amino acid sequence represented by QGLRRRGAMDY (SEQ ID NO 9). In a preferred embodiment, a variable region of the heavy chain comprises an amino acid sequence represented by SEQ ID NO 10, i.e., positions 20-139 of SEQ ID NO 11.

In another preferred embodiment of the present invention, the antibody or its antigen-binding fragment comprises light chain variable regions and heavy chain variable regions. A variable region of the light chain comprises: CDR1 comprising an amino acid sequence represented by ASQSVDYDGDVFL (SEQ ID NO 2) CDR2 comprising an amino acid sequence represented by YAASN (SEQ ID NO 3), and CDR3 comprising an amino acid sequence represented by QSNEVPWT (SEQ ID NO 4) and a variable region of the heavy chain comprises: CDR1 comprising an amino acid sequence represented by SGFTFSSFG (SEQ ID NO 7), CDR2 comprising an amino acid sequence represented by ISNGGS (SEQ ID NO 8), and CDR3 comprising an amino acid sequence represented by QGLRRRGAMDY (SEQ ID NO 9).

In the above embodiment, a more favorable example is an antibody or its antigen-binding fragment comprises a light chain variable region and a heavy chain variable region, wherein the light chain variable region comprises an amino acid sequence represented by positions 21-131 of SEQ ID NO 6, i.e., SEQ ID NO 5, and the heavy chain variable region comprises an amino acid sequence represented by positions 20-139 of SEQ ID NO 11, i.e., SEQ ID NO 10.

According to the embodiments of the present invention, the monoclonal antibody is preferably a chimeric antibody, a humanized antibody or a human antibody.

In the preferred embodiments of the invention, the antigen-binding fragment may be Fab, Fab', (Fab') 2, Fv or scFv. The immunoglobulin isotype may be IgG1, IgG2, IgG4, IgA, IgE or IgD.

The present invention also provides a hybridoma for producing the monoclonal antibody of the present invention, or its antigen-binding fragment. In the preferred embodiments of the invention, the hybridoma is hybridoma 9E4.

The monoclonal antibody and its antigen-binding fragment as well as the hybridoma of the invention may be prepared in accordance with the following steps: using a peptide comprising an amino acid sequence represented by MEKVGKDGVITVE (SEQ ID NO 1) as an antigen to cause a mammal to generates an immune response to the antigen; obtaining a plasma cell (immune cell) from the mammal immunized against the pathogens and fusing the obtained immune cell with a mammalian myeloma cell to produce a hybridoma; cloning the obtained hybridoma to obtain a desired hybridoma. The method of the present invention may further comprise the steps of: using the obtained hybridoma to produce antibodies; and harvest the antibodies produced by the hybridoma.

In the above-described method, method of immunizing a mammal may be any administration method known in the art. Suitable methods include: intraperitoneal injection, spleen injection, intramuscular injection, subcutaneous injection, intradermal injection, oral administration, mucosal administration, transdermal administration and the like. Among them, intraperitoneal injection and spleen injection are preferred. Intervals of the administration of the antigen may be determined in accordance with total amount of antigen administered, specie of the mammals and other conditions, such as several times a month.

The immunized mammalian is not limited to particularly species. However, choice shall be made taking into consideration conditions such as compatibility of myeloma cells used in the cell fusion. Suitable mammals include mice, rats and hamsters. Among them, mice are preferred.

The immune cells are preferably spleen cells but this is not any technical limitation.

Immune cells are fused with myeloma cells, using any of the known methods. Suitable methods include one proposed by Milstein et al. (Methods Enzymol., 73, 3-46, 1981). The method comprises the steps of: in the presence of a fusion accelerator, mixing the immune cells with myeloma cells in a culture medium. Additional culture media are appropriately added in the process of cell fusion. Separate by centrifugation repeatedly to obtain hybridomas.

Suitable culture media for use in the cell fusion include: RPMI-1640 medium, MEM medium and the like. These media are often used in cell fusion. In the fusion process supplements such as serum, e.g. fetal calf serum may be added when appropriate.

In general, temperature for the cell fusion is preferably 25-37° C., more preferably 30-37° C. The ratio of the immune cells and the myeloma cells is preferably between about 1:1 to about 1:10.

Suitable fusion accelerators include: polyethylene glycol (PEG), Sendai virus (HVJ) and the like. Among them, PEG is preferred. If PEG is used, its molecular weight may be appropriately selected, for example, an average molecular weight of about 1,000 to about 6,000. Furthermore, the concentration of the PEG in the medium can range from about 30 to about 60% (W/V).

In the method described above, the hybridomas may be chosen, with the steps of: Hybridomas obtained by the cell fusion are cultured in a culture medium. The medium is preferably a selective medium, such as HAT medium and other commercially available media. Limiting dilution method is used to screen the obtained hybridomas, using, for example, antibody values of peptide including an amino acid sequence represented by MEKVGKDGVITVE (SEQ ID NO. 1) as an indicator. Cultivation time must be long enough to cause cells other than the target hybridomas death and is usually several days to several weeks. Hybridomas obtained from these steps may be provided for subculture in conventional culture media, or for long-term preservation in liquid nitrogen.

In the invented method, harvest of the monoclonal antibody or its antigen binding fragments of the present invention comprises the steps of: Use a known method to culture the hybridomas; and obtain monoclonal antibodies from their culture supernatant. Another method includes the steps of: administer the hybridomas to mammals adaptive to the hybridomas for proliferation of the hybridomas; and obtain monoclonal antibodies from ascites of the mammal. Among the applicable methods, obtaining monoclonal antibodies from culture supernatant produces higher purity of antibodies, while obtaining monoclonal antibodies from ascites enables mass production of antibodies. Those having ordinary skills in the art may properly choose a method in accordance with the purpose of harvest.

Monoclonal antibodies or antigen-binding fragment thereof obtained from the above steps may be further purified. The purification process may be any of the known methods, e.g., salt fractionation, gel filtration, affinity chromatography and the like.

The invented monoclonal antibodies and their antigen-binding fragment perform significant functional inhibition effects against the immunosuppressive functions of the pathogens. In application, the invented monoclonal antibody or its antigen-binding fragments can be administrated directly, or as a pharmaceutical composition that includes pharmaceutically acceptable additives etc. According to the present invention, the pharmaceutical composition comprises an effective dose of the monoclonal antibody, or antigen-binding fragment thereof, of the present invention. The pharmaceutical composition may be used as a functional inhibitor against immunosuppressive functions of particular pathogens. The present invention also provides use of the invented monoclonal antibody, including in the preparation of a pharmaceutical composition.

The pharmaceutical composition of the present invention is a composition comprising an function inhibitor that inhibits immunosuppressive functions and is prepared by the steps of: Diluting or suspending the monoclonal antibody or its antigen-binding fragment of the present invention in a physiological saline, distilled water, or a buffer solution such as an injection buffer liquid; and modulating to obtain the composition. The immunosuppressive function inhibitor composition of the present invention may comprise other additives. Suitable additives include: solvents, dissolution aids, preservatives, stabilizers, emulsifiers, suspending agents, soothing agents, isotonic agents, buffers, excipients, thickening agents, coloring agents, and conventional carriers such as various ribosome, poly amino acid carrier, synthetic polymers, natural polymers and so on.

According to the present invention, a method to suppress immune suppressions caused by heat shock protein 60 secreted by pathogens such as *H. pylori* or other similar bacteria, is provided. After a living host is administered with the monoclonal antibody of the present invention or its antigen-binding fragment, the immune suppressions caused by the heat shock protein 60 of the pathogens is inhibited, whereby the immune system of the living host is activated and the pathogens are eliminated.

In the invented method, the monoclonal antibody of the present invention or its antigen-binding fragment may be administered to the host systemically or locally. The method of administration includes any of the known methods, e.g., drip, intravenous injection, intramuscular injection, subcutaneous injection, intradermal injection, oral administration, mucosal administration, transdermal administration and the like.

The effective amount of the invented monoclonal antibody or its antigen-binding fragment is not any technical limitation. Those having ordinary skills in the art may determine appropriately in accordance with type, nature, sex and age etc. of the host.

In the followings, certain examples will be described by referring to the drawings, in order to illustrate the monoclonal antibody inhibiting immunosuppressive functions of pathogens, antigen-binding fragment thereof, and hybridomas producing such antibody, of this invention. It is however appreciated that the scope of this invention is not limited to any of the embodiments described. For example, although in the detailed description the pathogenesis mechanism of *H. pylori* and functional inhibitor for HpHSP60 are used as examples in the description of the invention, the heat shock protein of other bacteria, such as *Helicobacter felis* (known cause of chronic enteritis) and *Arcobacter suis* (known cause of periodontal disease), also include an identical fragment of HpHSP60, such as HSP 60 101-200. Therefore, the method and use of this invention are also useful in these and other pathogenesis bacteria, and other pathogens that have similar pathogenesis mechanism.

Embodiment 1: Cell Culture and Isolation of PBMC and T-Cells

Human peripheral blood mononuclear cells (PBMCs) from healthy donors were isolated by density gradient centrifugation using Ficoll-Paque Plus (GE Healthcare, Uppsala, Sweden) and resuspended in RPMI-1640 with 10% inactivated fetal calf serum and 1% penicillin-streptomycin. For monocyte depletion, PBMCs were cultured in 10-cm dishes at a density of $10^6$/ml overnight for monocyte attachment. The suspended cells were then collected by centrifugation at 1500 rpm for 15 min. Total T-cells were isolated from PBMCs by negative selection using a magnetic sorting device (Miltenyi Biotec, MA, USA). Briefly, PBMCs were incubated with a cocktail of biotin-conjugated antibodies, followed by microbead-conjugated anti-biotin Abs for magnetic depletion. T-cells were eluted according to the manufacturer's protocols.

Embodiment 2: The Effect of HpHSP60 on PBMC Proliferation

Proliferation of anti-CD3 mAb-stimulated PBMCs treated with HpHSP60, rGFP or boiled HpHSP60 at different doses was monitored by a cell proliferation assay. To measure cell proliferation, 0.2 ml of cells at 1×106 cells/ml were seeded in each well of an anti-CD3 mAb-precoated 96-well microplate. Cell proliferation was determined by an MTT assay after 96 hours. Results are shown in FIG. 1: experimental results on effects of HpHSP60 on PBMC proliferation. Data shown therein are reported as the proliferation index.

The cell proliferation index was calculated as follows: Proliferation index (100%)=($OD_{595}$ of the anti-CD3+HpHSP60-treated cells)/($OD_{595}$ of the anti-CD3-treated cells)*100%. The results that differ significantly from the untreated group are indicated by * ($p<0.05$) (n=15).

In FIG. 1, (♦) shows proliferation of T-cells is inhibited, after HpHSP60 is added into the PBMC. (■) shows rGFP, being a control protein in this experimental system, does not influence T-cell proliferation. The results of this control unit show that not any protein is capable of inhibiting T-cell proliferation. (▲) represents boiled HpHSP60, which includes the sequence of HpHSP60, while its protein structure has been destructed. The results show that boiled HpHSP60 does not influence T-cell proliferation.

Embodiment 3: Influence of HpHSP60 on T-Cell Proliferation in PBMC

After treatment with anti-CD3 mAb, PBMCs were treated with or without HpHSP60 (200 ng). T-cells or non-T-cells in PBMCs were identified by CD3 surface marker staining. Cell number was then calculated following a flow cytometer analysis.

For CD3 surface marker staining, cells were harvested and stained with 1 μg mouse anti-human CD3 IgG mAbs (OKT3), followed by 0.5 μg rabbit anti-mouse IgG-FITC secondary Abs (Biolegend, CA, USA). For FoxP3 intracellular staining, the cells were harvested and stained with mouse anti-human CD4-FITC mAbs (Biolegend, CA, USA) prior to fixing and permeabilization, followed by intracellular staining with mouse anti-human FoxP3-PE mAbs (BD Biosciences, MA, USA) according to the manufacturer's protocol. For the cell cycle assay, cells were harvested after 72 hours and $10^6$ cells were fixed with 70% ice-cold ethanol. DNA was stained with DNA staining buffer (5% Triton-X 100, 0.1 mg/ml RNase A, and 4 μg/ml propidium iodide) for 30 min at room temperature. Changes in the DNA content were then detected. Fluorescence was analyzed using a FACS flow cytometer (Becton Dickinson, Heidelberg, Germany) and CELLQuest Pro software (Becton Dickinson, Heidelberg, Germany). Results are shown in FIG. 2: experimental results on effects of HpHSP60 on T-cell proliferation.

Figure 2:
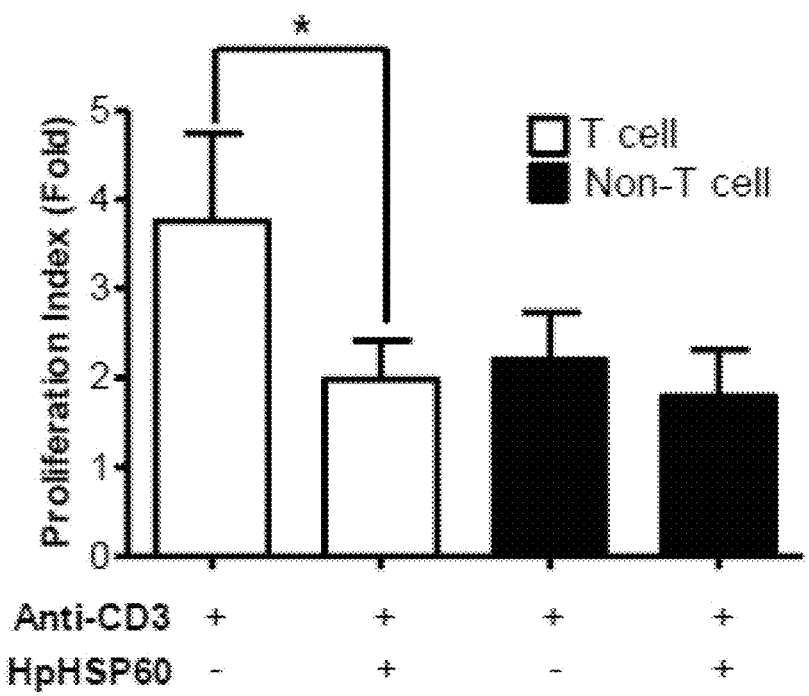
FIG. 2 shows experimental results on effects of HpHSP60 on T-cell proliferation.

In FIG. 2, the proliferation index is calculated as: proliferation index (fold)=(number of T- or non-T-cells in the anti-CD3/HpHSP60-treated group)/(number of T- or non-T-cells in the untreated control). A significant difference is indicated by *($p<0.05$) (n=4). The results show that HpHSP60 is capable of inhibiting the proliferation of T-cells. In this figure, (□) represents T-cells in PBMC. (■) represents non-T-cells in PBMC. Clearly, what HpHSP60 inhibits is the proliferation of T-cells.

Embodiment 4: Effects of HpHSP60 on the Cell Cycle

Figures 3A, 3B, 3C:
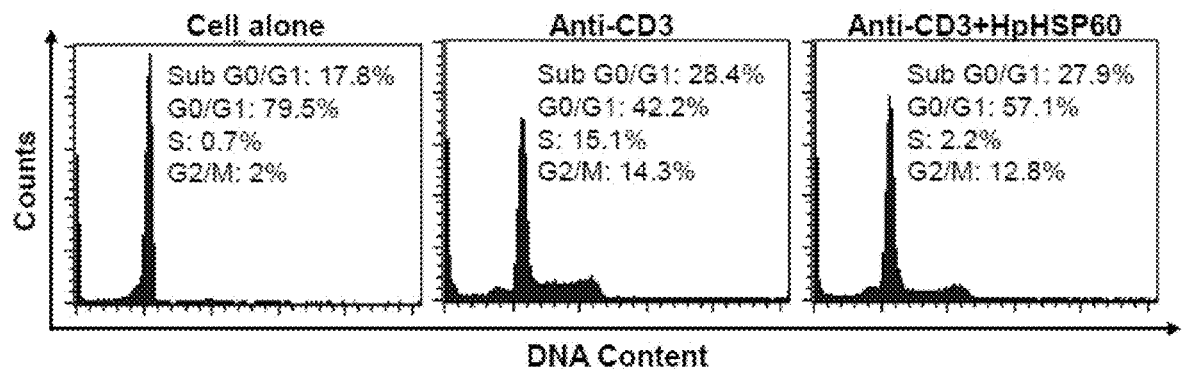
FIGS. 3A-3C respectively show experimental results on effects of HpHSP60 on PBMC cell cycles.

The effects of HpHSP60 on the cell cycle of PBMC were determined. From the PBMC products of Embodiment 3, PBMCs alone, CD3-activated PBMCs and PBMCs treated with anti-CD3 and HpHSP60 are obtained respectively. The percentages of cells in the sub-G1, G1, S, and G2/M phases are observed and presented in histogram plots, as shown in FIG. 3A-3C. FIGS. 3A-3C respectively show experimental results on effects of HpHSP60 on PBMC cell cycles. The figures are representative of three replicates.

FIGS. 3A-3C show that HpHSP60 inhibits the proliferation of T-cells, rather than causing them death. FIG. 3A shows T-cells without CD3 activation (Cell alone) remain in their dormant phases (G0/G). FIG. 3B shows that, after activation by CD3, the T-cells' growth was activated and the typical cell cycle graphics are formed. FIG. 3C shows no substantial difference with FIG. 3B. PBMCs treated with anti-CD3 and HpHSP60 (Anti-CD3+HpHSP60) exhibit the same ratio at the sub G0/G1 phases (representing death of cells) as that of the Anti-CD3 group. The experimental results show that the role of HpHSP60 is to inhibit the growth of T cells, rather than resulting in death.

Embodiment 5: Results of Treg Cells In Vitro Induction by HpHSP60

The proportions of $CD4^+FoxP3^+$ cells in HpHSP60-treated PBMCs were measured over time. A significant difference compared to the anti-CD3 control is indicated by *($p<0.05$) (n=5). The results are shown in FIG. 4: experimental results on Treg cells in vitro induction by HpHSP60.

Figure 4:
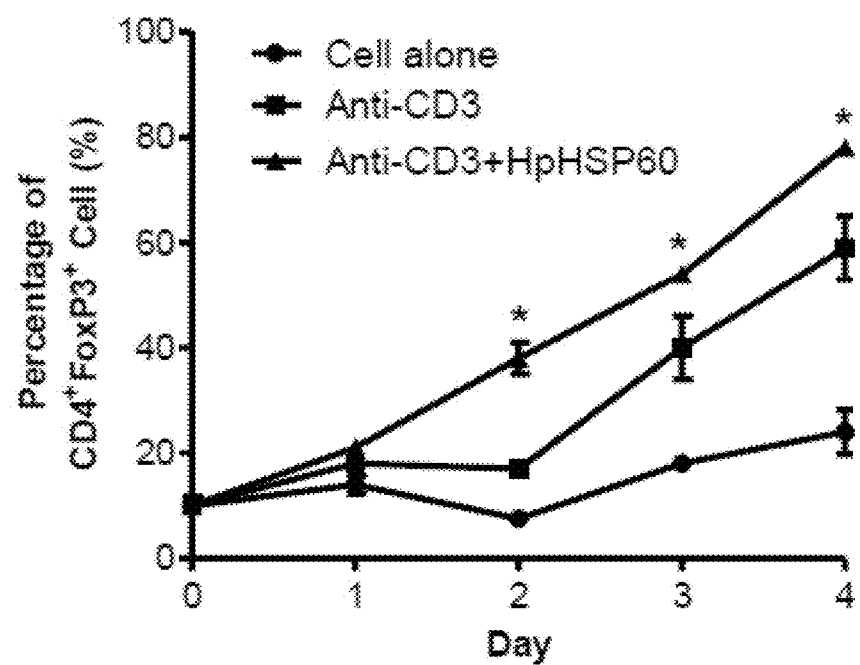
FIG. 4 shows experimental results on Treg cells in vitro induction by HpHSP60.

Since CD4 and FoxP3 are markers for Treg cells, it is possible to identify HpHSP60's effects in T-cell growth from FIG. 4. In this figure, "(•) cell alone" expresses the original growth curve of T-cells. "(■) anti-CD3" expresses the growth curve of T-cells activated by CD3. "(▲) Anti-CD3+HpHSP60" shows a significant proliferation of T-cells. The experimental results show that HpHSP60 is capable of enhancing Treg cell proliferation.

Embodiment 6: HpHSP60 Enhances Treg Cell Proliferation

Figure 5:
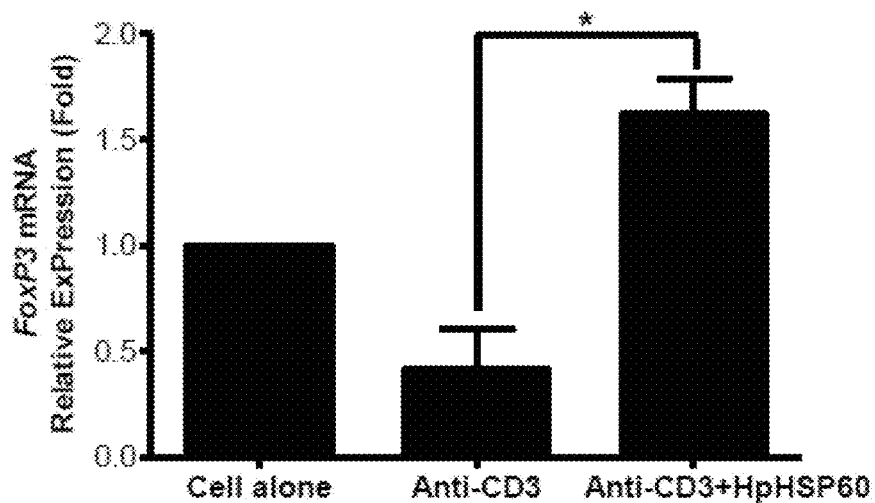
FIG. 5 shows experimental results on effects of HpHSP60 on Treg cell proliferation.

Following Embodiment 5, cells were harvested after 72 hours for total RNA isolation. Real-time PCR was used to measure the expression of FoxP3 mRNA. A significant difference compared to the anti-CD3 control is indicated by *($p<0.05$) (n=4). The results are shown in FIG. 5: experimental results on effects of HpHSP60 on Treg cell proliferation.

Since FoxP3 is marker for Treg cells. When Treg cells are activated, expression of FoxP3 also increases. The mRNA assay results of FIG. 5 show that, following the addition of HpHSP60, FoxP3 expression significantly increases. This experiment further supports the fact that adding HpHSP60 enhances Treg cell proliferation.

Figure 6:
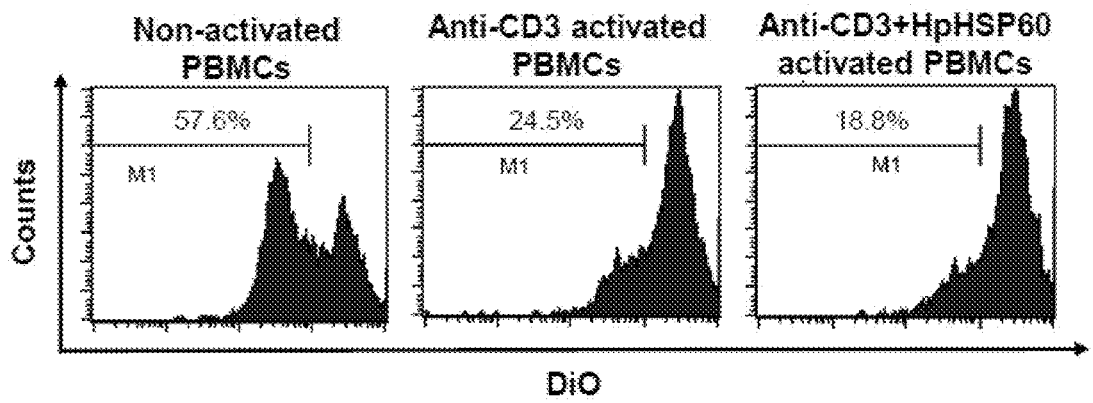
FIG. 6 shows experimental results on effects of HpHSP60-induced Treg cells on T-cell proliferation.

Embodiment 7: The Activity of HpHSP60-Induced Treg Cells on T-Cell Proliferation Functional assay is used to measure the activity of HpHSP60-induced Treg cells on cell proliferation. The results are shown in FIG. 6. FIG. 6 shows experimental results on effects of HpHSP60-induced Treg cells on T-cell proliferation. Numbers on the histogram plots indicate the percentage of proliferative cells. The histogram plot is representative of three replicates.

The experimental results show that, when number of Treg cells increases, activities of T-cells are correspondingly inhibited. This proves that when HpHSP60 is added in the PBMC, activities of T-cells are inhibited, due to increase of Treg cells.

Embodiment 8: Preparation of Anti-HpHSP60 Serum and HpHSP60 Monoclonal Antibodies C3H/HeN mice were purchased from the National Laboratory Animal Breeding and Research Center, Taipei, Taiwan, and maintained in pathogen-free isolators. All food, water, caging, and bedding were sterilized before use. Male 5-week-old mice were i.v. injected with HpHSP60 to generate immunization reactions. After repeated boost of HpHSP60, blood of the mice is collected. Serum is isolated to obtain anti-HpHSP60 antibody containing serum, referred to as "anti-HpHSP60 serum." The products of this step are the polyclonal antibody The spleen cells of the mice were fused with mouse myeloma cells to form a hybridoma. The products are further screened by enzyme immunoassay (ELISA) to isolate specific antibodies.

The resulting cell lines were diluted and re-distributed into a cell culture plate with 96 wells. Calculate to ensure that each well contains only one cell. After the cells grow to form colonies, the colonies are again screened by ELISA to obtain specific antibodies. Monoclonal antibodies are thus obtained.

Embodiment 9: Assessment of the Eradication of H. pylori by Blockage of HSP60 In Vivo C3H/HeN mice were purchased from the National Laboratory Animal Breeding and Research Center, Taipei, Taiwan, and maintained in pathogen-free isolators. All food, water, caging, and bedding were sterilized before use. Male 5-week-old mice were i.v. injected with 0.1 ml anti-HSP60 serum obtained from Embodiment 8 before H. pylori inoculation. At 24 hours after the anti-serum treatment, the mice were infected 0.5 mL live H. pylori (ATCC 15415 strain, approximately $10^9$ colony-forming units) in BHI broth by oral gavage twice within a 3-day period. After infection with H. pylori was established, the mice were then i.v. injected with 0.1 ml anti-HSP60 serum every 3 days.

At the 8th weeks after H. pylori inoculation, all of the mice were sacrificed aseptically and the intact stomachs were opened along the lesser curvature. Each stomach was dissected into two equal longitudinal specimens, containing the gastric body and antrum. The eradication of H. pylori was analyzed by H. pylori re-culture and immunohistochemistry staining for the expression of FoxP3.

Figure 7:
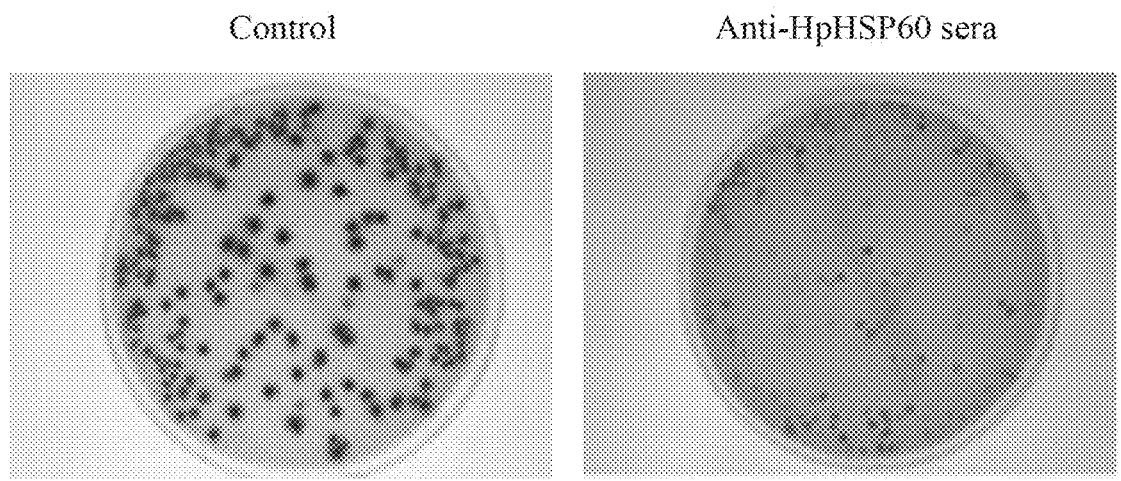
FIG. 7 shows experimental results on inhibition of *H. pylori* in vivo growth due blockage of HpHSP60 immunosuppressive functions.
Figure 8:
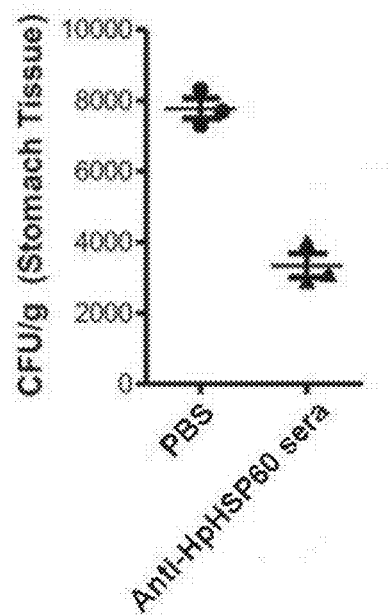
FIG. 8 shows results of another experiment on inhibition of *H. pylori* in vivo growth due blockage of HpHSP60 immunosuppressive functions.
Figure 9:
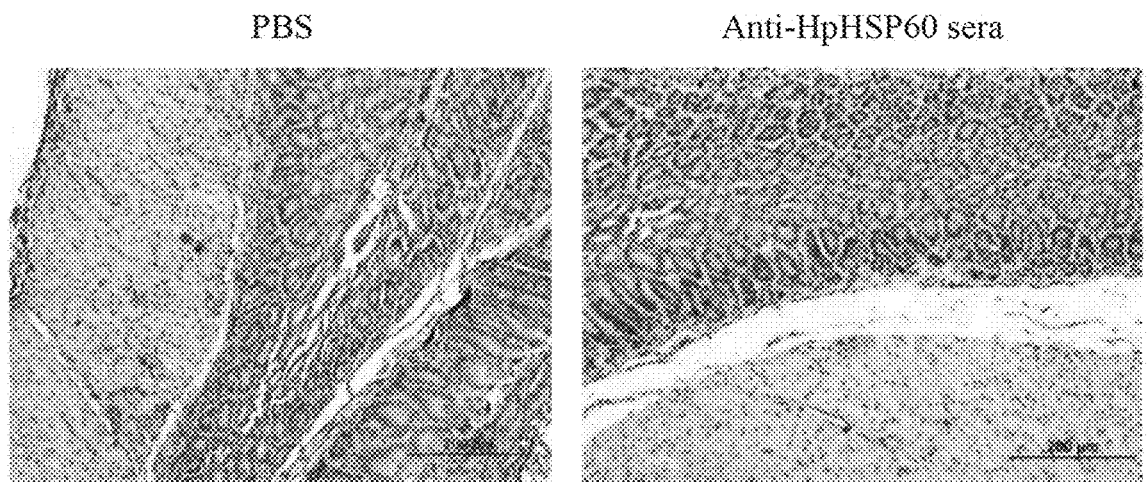
FIG. 9 shows experimental results on inhibition of Treg cells due blockage of HpHSP60 immunosuppressive functions.

The results are presented as the mean±SEM. The statistical significance was evaluated using the one-tailed Student's t-test; p<0.05 was considered significant. The results are shown in FIGS. 7, 8 and 9. Among them, FIGS. 7 and 8 respectively show results of several experiments on inhibition of H. pylori in vivo growth due blockage of HpHSP60 immunosuppressive functions. FIG. 9 shows experimental results on inhibition of Treg cells due blockage of HpHSP60 immunosuppressive functions.

FIGS. 7 and 8 show that the anti-HpHSP60 serum significantly reduces the re-culture of H. pylori colonies from a gastric tissue lysate at the $8^{th}$ week after H. pylori inoculation. To determine the mechanism of colony decrease by antibodies, the expression of Treg cells in H. pylori-infected gastric tissues was evaluated. FIG. 9 reveals that the anti-HpHSP60 serum treatments significantly reduce the expression of Treg cells in the gastric mucosa. These results indicate that chronic H. pylori infection is correlated with HpHSP60 and that the blockage of HpHSP60 can decrease H. pylori colonization and the generation of Treg cells.

Embodiment 10: Positions of Treg Cell Inducible Sequence in HpHSP60

In order to allocate the position of active sequence in HpHSP60 that induces Treg cells, anti-HpHSP60 mAbs that recognize the full sequence or fragments of HpHSP60 are prepared. The method of Embodiment 9 is used. After 24-h treatment with the anti-HpHSP60 serum, the mice were infected by H. pylori, whereby infection of H. pylori Is established. The mice were then i.v. injected with 0.1 ml PBS, serum, anti-HSP60 serum, LHP-1 (9E4) mAb and LHP-2 (5A8) mAb, respectively, every 3 days. Mice were sacrificed after 8 weeks. The gastric wall was ground and the obtained gastric homogenates were incubated in H. pylori incubated isolation medium (EYE agar), to confirm H. pylori parasites in stomach. The results are shown in FIG. 10: experimental results on active sequence in HpHSP60 that induces Treg cells growth.

Figure 10:
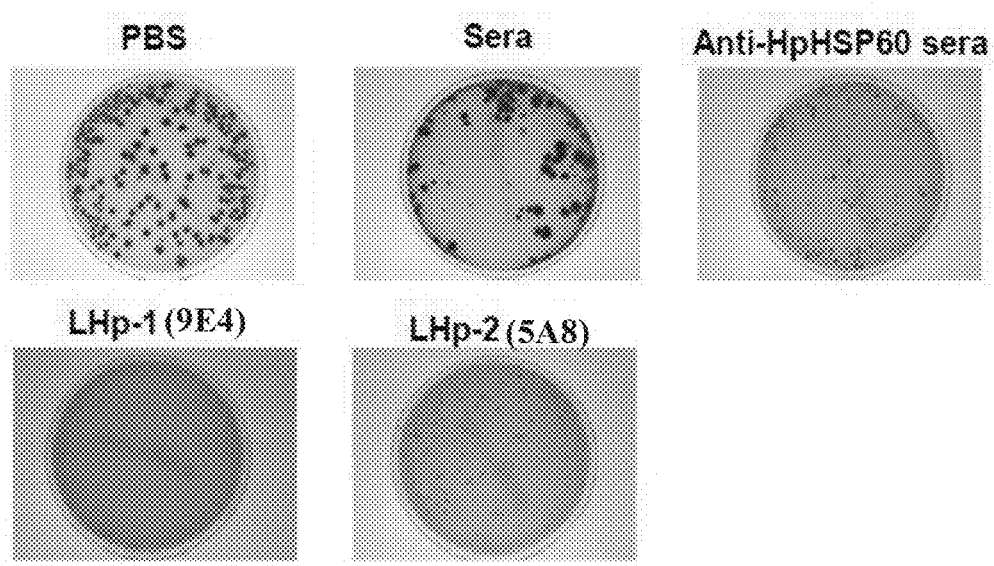
FIG. 10 shows experimental results on active sequence in HpHSP60 that induces Treg cells growth.

As shown in FIG. 10, the red spots on the plate are colonies of H. pylori. This experiment reveals that, while anti-HpHSP60 serum inhibits growth of H. pylori, LHP-1 (9E4) antibody is capable of completely eliminating H. pylori.

Figure 11:
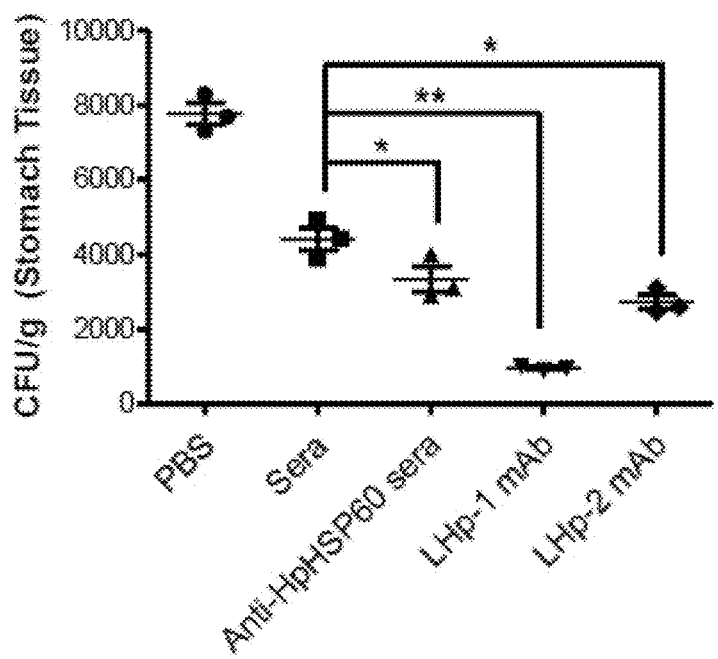
FIG. 11 shows quantization of experimental results shown in FIG. 10.

Number of H. pylori colonies (CFU) was determined by counting the red colonies on the EYE plate. A significant different is indicated by *(p<0.05). The results are shown in FIG. 11. FIG. 11 shows quantization of experimental results shown in FIG. 10. As shown in FIG. 11, H. pylori was completely eliminated after the LHP-1 (9E4) antibody was added.

Embody 11: Immunological Mechanisms of Anti-HpHSP60 Antibody

Figure 12:
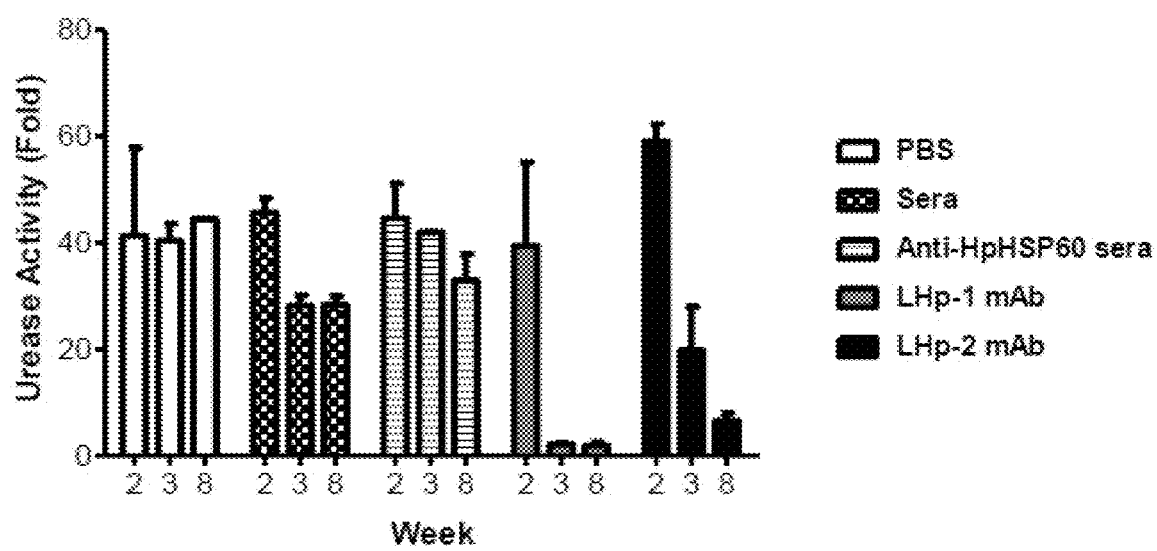
FIG. 12 shows experimental results on a study of the immunological mechanism of anti-HpHSP60 antibodies.

In order to understand immunological mechanisms of anti-HpHSP60 antibody, gastric urease activity of the mice according to Embodiment 10 at the $2^{nd}$, $3^{rd}$ and $8^{th}$ week after H. pylori inoculation was measured. The urease activity is normalized to the gastric urease activity of the control mice (without H. pylori infection). The results are shown in FIG. 12: experimental results on a study of the immunological mechanism of anti-HpHSP60 antibodies. This figure shows that the LHP-1 (9E4) antibody inhibits growth of H. pylori, or even eliminates H. pylori, by inhibiting the activity of HpHSP60.

The LHP-1 (9E4) antibody was generated by using the amino acid sequence of positions 101 to 200 of HpHSP60 as antigen. Hybridomas including this antibody, LHP-1 (9E4), were deposited with the American Type Culture Collection (ATCC®), Manassas, Va., USA, ATCC Accession Number: PTA-122900.

Embodiment 12: Evaluation of Expression of Treg Cells in Gastric Mucosa

Figure 13:
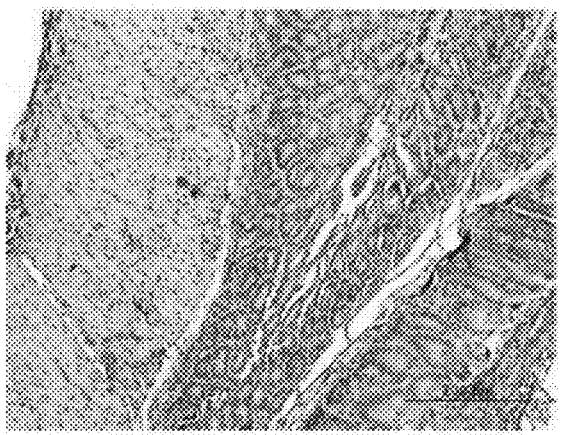
FIG. 13 shows experimental results on effects of anti-HpHSP60 antibodies on Treg cells expressions in mice gastric mucosa.
Figure 13:
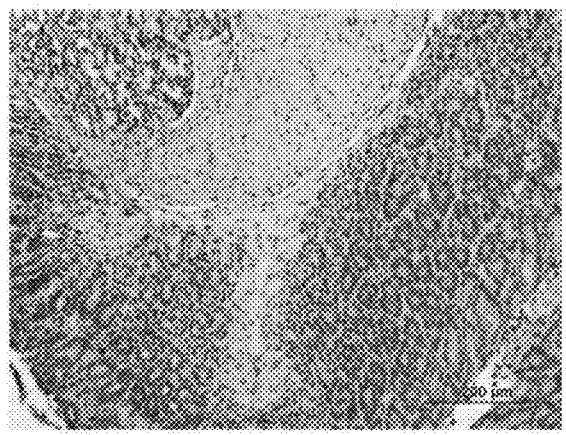
Figure 13:
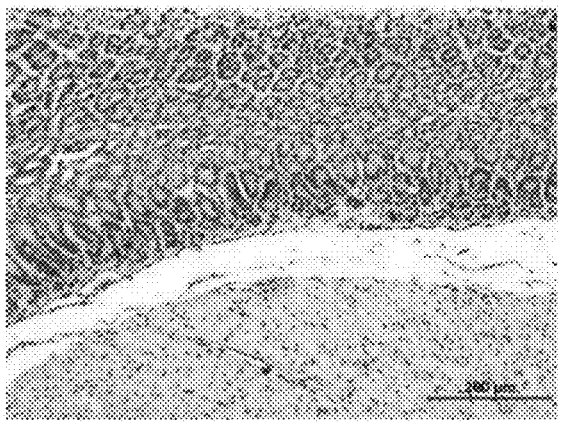
Figure 13:
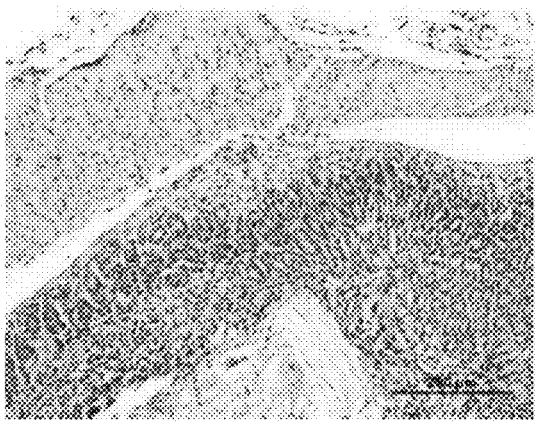
Figure 13:
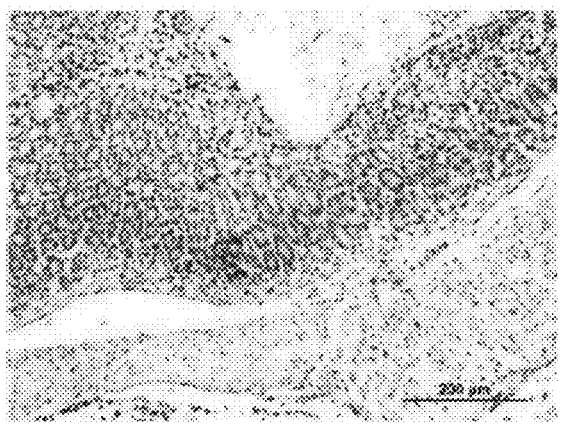

In order to understand anti-HpHSP60 antibody's effects in the expression of Treg cells in gastric mucosa, mouse stomachs obtained in Embodiment 10 were fixed with neutral buffered 10% formalin and embedded in paraffin. Five-micrometer sections were stained with H&E stain, followed by immunohistochemistry staining of FoxP3. The results are shown in FIG. 13. FIG. 13 shows experimental results on effects of anti-HpHSP60 antibodies on Treg cells expressions in mice gastric mucosa. In this figure, all pictures are representative of the mice sacrificed at the 8$^{th}$ week (200 μm original magnification ×100). The results show that no Treg expressions are observed in the mice gastric mucosa that was treated with LHP-1 (9E4) antibodies.

Embodiment 13: Effects of HpHSP60 in Expression of IL-10 in Mice Gastric Mucosa

Figure 14:
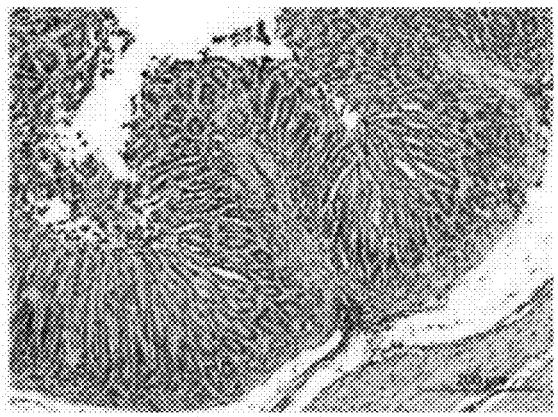
FIG. 14 shows experimental results on effects of anti-HpHSP60 antibodies on IL-10 expressions in mice gastric mucosa.
Figure 14:
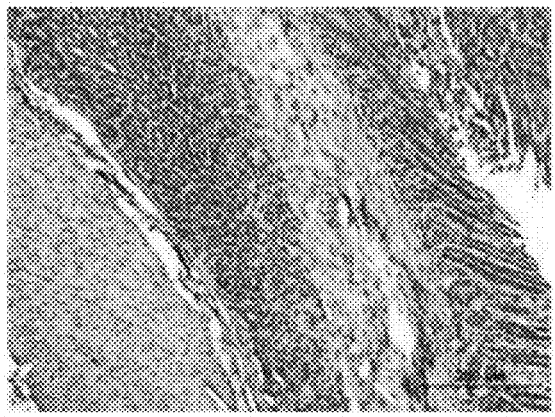
Figure 14:
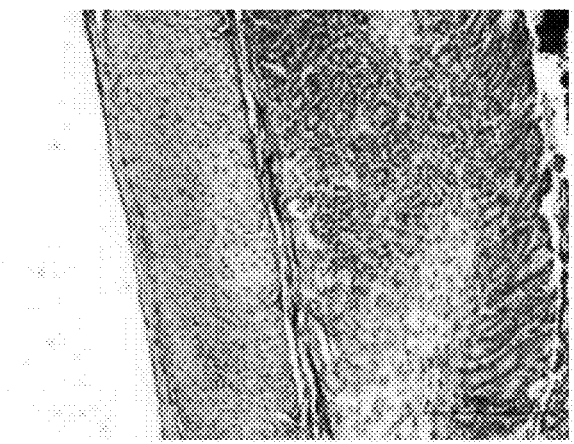
Figure 14:
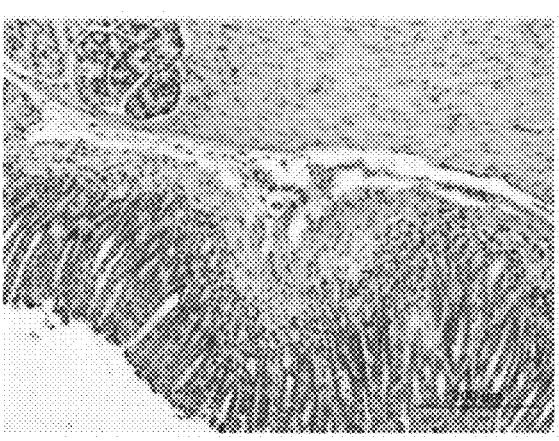
Figure 14:
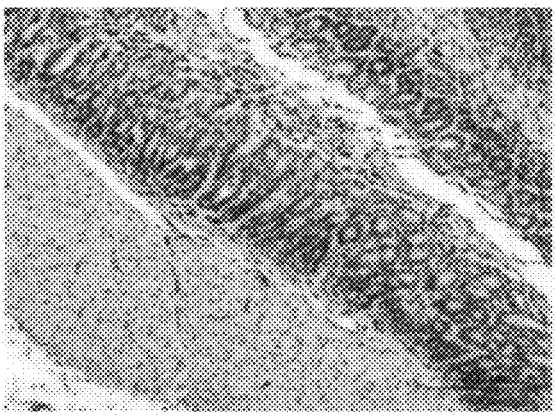

Mouse stomachs obtained in Embodiment 10 were fixed with neutral buffered 10% formalin and embedded in paraffin. Five-micrometer sections were stained with H&E stain, followed by immunohistochemistry staining of IL-10. The results are shown in FIG. 14. FIG. 14 shows experimental results on effects of anti-HpHSP60 antibodies on IL-10 expressions in mice gastric mucosa. In this figure, all pictures are representative of the mice sacrificed at the 8$^{th}$ week (200 μm original magnification ×100; 100 μm original magnification ×200). The results show that no IL-10 expressions are observed in the mice gastric mucosa that was treated with LHP-1 (9E4) antibodies.

Embodiment 14: Fragments of HpHSP60 Identifiable by LHP-1 (9E4) Antibody

Figure 15:
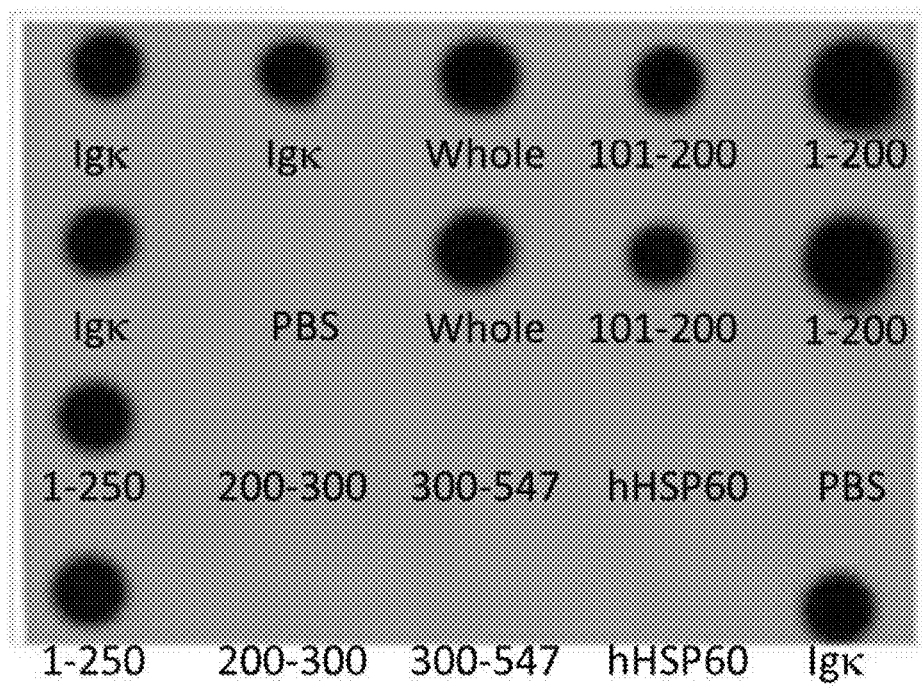
FIG. 15 shows experimental results on recognition of HpHSP60 fragments by LHP-1 (9E4) antibody.

The LHP-1 (9E4) antibody is used to identify different lengths of fragments of HpHSP60, to determine fragments of HpHSP60 that can be recognized by the LHP-1 (9E4) antibody. The results are shown in FIG. 15. FIG. 15 shows experimental results on recognition of HpHSP60 fragments by LHP-1 (9E4) antibody. In this figure, dark spots represent positive identifications. Fragments being identified include the followings, while IgK is used as positive controls, since most mice mAbs are kappa type:

Whole—the full length of HpHSP60, i.e. positions 1-547.

1-200—fragment including positions 1-200 of HpHSP60.
101-200—fragment including positions 101-200 of HpHSP60.
1-250—fragment including positions 1-250 of HpHSP60.
200-300—fragment including positions 200-300 of HpHSP60.
300-547—fragment including positions 300-547 of HpHSP60.

The results show that the HpHSP60 fragment identifiable by the LHP-1 (9E4) antibody is the sequence of positions 101-200, which amino acid sequence is:

```
                                             (SEQ ID NO 12)
EGLRNITAGANPIEVKRGMDKAAEAIINELKKASKKVGGKEEITQVATIS

ANSDHNIGKLIADAMEKVGKDGVITVEEAKGIEDELDVVEGMQFDRGYLS
```

Figure 16:
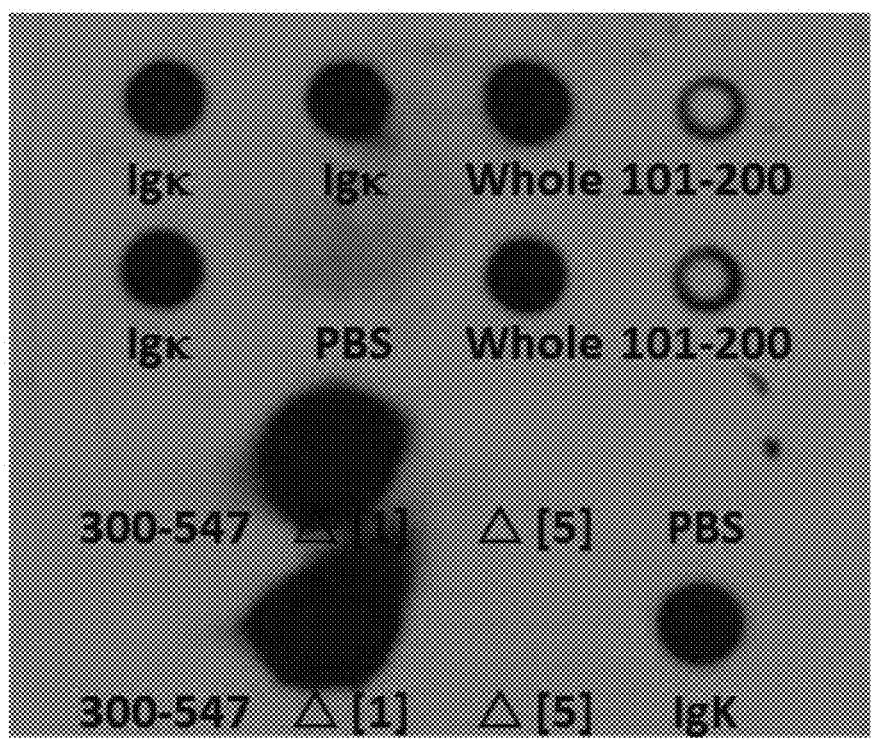
FIG. 16 shows results of further experiments on recognition of HpHSP60 fragments by LHP-1 (9E4) antibody.

Embodiment 15: Further Limitation of HpHSP60 Fragment Identifiable by LHP-1 (9E4) Antibody Following the method of Embodiment 14, use the LHP-1 (9E4) antibody to identify different fragments with shorter lengths. The results are shown in FIG. 16. FIG. 16 shows results of further experiments on recognition of HpHSP60 fragments by LHP-1 (9E4) antibody. In this figure, dark spots represent positive identifications. Δ[1] represents positions 134-200 of HpHSP60, with positive results, while Δ[5] represents positions 101-168 of HpHSP60, with negative results. It can therefore be concluded that the HpHSP60 fragment identifiable by the LHP-1 (9E4) antibody includes amino acid positions 169-200 of HpHSP60, which are:

```
                                             (SEQ ID NO 13)
KDGVITVEEAKGIEDELDVVEGMQFDRGYLS.
```

What is claimed is:

1. A hybridoma deposited with the American Type Culture Collection having the ATCC Accession Number: PTA-122900.

2. A method of producing a monoclonal antibody comprising culturing the hybridoma of claim 1 and harvesting the antibodies produced by the hybridoma.

* * * * *

SEQUENCE LISTING

```
<160> NUMBER OF SEQ ID NOS: 13

<210> SEQ ID NO 1
<211> LENGTH: 13
<212> TYPE: PRT
<213> ORGANISM: Mus musculus

<400> SEQUENCE: 1

Met Glu Lys Val Gly Lys Asp Gly Val Ile Thr Val Glu
1               5                   10

<210> SEQ ID NO 2
<211> LENGTH: 13
<212> TYPE: PRT
<213> ORGANISM: Mus musculus

<400> SEQUENCE: 2

Ala Ser Gln Ser Val Asp Tyr Asp Gly Asp Val Phe Leu
1               5                   10

<210> SEQ ID NO 3
<211> LENGTH: 5
<212> TYPE: PRT
<213> ORGANISM: Mus musculus

<400> SEQUENCE: 3

Tyr Ala Ala Ser Asn
```

```
1               5
```

<210> SEQ ID NO 4
<211> LENGTH: 8
<212> TYPE: PRT
<213> ORGANISM: Mus musculus

<400> SEQUENCE: 4

```
Gln Ser Asn Glu Val Pro Trp Thr
1               5
```

<210> SEQ ID NO 5
<211> LENGTH: 111
<212> TYPE: PRT
<213> ORGANISM: Mus musculus

<400> SEQUENCE: 5

```
Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Val Phe Leu Asn Trp Tyr Gln Gln Lys Pro Gly Gln Pro Pro
        35                  40                  45
Lys Leu Leu Ile Tyr Ala Ala Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Asp Ala Ala Thr Tyr Tyr Cys Gln Gln Ser Asn
                85                  90                  95
Glu Val Pro Trp Thr Phe Gly Gly Gly Thr Lys Leu Glu Ile Lys
            100                 105                 110
```

<210> SEQ ID NO 6
<211> LENGTH: 131
<212> TYPE: PRT
<213> ORGANISM: Mus musculus

<400> SEQUENCE: 6

```
Met Glu Thr Asp Thr Ile Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Arg Ala Thr Ile Ser Cys Lys Ala Ser Gln Ser
        35                  40                  45
Val Asp Tyr Asp Gly Asp Val Phe Leu Asn Trp Tyr Gln Gln Lys Pro
    50                  55                  60
Gly Gln Pro Pro Lys Leu Leu Ile Tyr Ala Ala Ser Asn Leu Glu Ser
65                  70                  75                  80
Gly Ile Pro Ala Arg Phe Ser Gly Ser Gly Ser Gly Thr Asp Phe Thr
                85                  90                  95
Leu Asn Ile His Pro Val Glu Glu Asp Ala Ala Thr Tyr Tyr Cys
            100                 105                 110
Gln Gln Ser Asn Glu Val Pro Trp Thr Phe Gly Gly Gly Thr Lys Leu
        115                 120                 125
Glu Ile Lys
        130
```

<210> SEQ ID NO 7

```
<211> LENGTH: 9
<212> TYPE: PRT
<213> ORGANISM: Mus musculus

<400> SEQUENCE: 7

Ser Gly Phe Thr Phe Ser Ser Phe Gly
1               5

<210> SEQ ID NO 8
<211> LENGTH: 6
<212> TYPE: PRT
<213> ORGANISM: Mus musculus

<400> SEQUENCE: 8

Ile Ser Asn Gly Gly Ser
1               5

<210> SEQ ID NO 9
<211> LENGTH: 11
<212> TYPE: PRT
<213> ORGANISM: Mus musculus

<400> SEQUENCE: 9

Gln Gly Leu Arg Arg Gly Ala Met Asp Tyr
1               5                   10

<210> SEQ ID NO 10
<211> LENGTH: 120
<212> TYPE: PRT
<213> ORGANISM: Mus musculus

<400> SEQUENCE: 10

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
                20                  25                  30

Gly Met Ser Trp Val Arg Gln Thr Pro Asp Lys Arg Leu Glu Trp Val
            35                  40                  45

Ala Thr Ile Ser Asn Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Gln Gly Leu Arg Arg Gly Ala Met Asp Tyr Trp Gly Gln
            100                 105                 110

Gly Thr Ser Val Thr Val Ser Ser
        115                 120

<210> SEQ ID NO 11
<211> LENGTH: 463
<212> TYPE: PRT
<213> ORGANISM: Mus musculus

<400> SEQUENCE: 11

Met Asn Phe Gly Leu Ser Leu Ile Phe Leu Ala Leu Ile Leu Lys Gly
1               5                   10                  15

Val Gln Cys Glu Val His Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45
```

-continued

Ser Ser Phe Gly Met Ser Trp Val Arg Gln Thr Pro Asp Lys Arg Leu
    50              55                  60

Glu Trp Val Ala Thr Ile Ser Asn Gly Gly Ser Tyr Thr Tyr Tyr Pro
65              70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Thr Arg Gln Gly Leu Arg Arg Gly Ala Met Asp Tyr
        115                 120                 125

Trp Gly Gln Gly Thr Ser Val Thr Val Ser Ser Ala Lys Thr Thr Pro
        130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285

Val Gln Phe Ser Trp Phe Val Asp Asp Val Glu Val His Thr Ala Gln
290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Lys
450                 455                 460

```
<210> SEQ ID NO 12
<211> LENGTH: 100
<212> TYPE: PRT
<213> ORGANISM: Helicobacter pylori

<400> SEQUENCE: 12

Glu Gly Leu Arg Asn Ile Thr Ala Gly Ala Asn Pro Ile Glu Val Lys
1               5                   10                  15

Arg Gly Met Asp Lys Ala Ala Glu Ala Ile Ile Asn Glu Leu Lys Lys
            20                  25                  30

Ala Ser Lys Lys Val Gly Gly Lys Glu Glu Ile Thr Gln Val Ala Thr
        35                  40                  45

Ile Ser Ala Asn Ser Asp His Asn Ile Gly Lys Leu Ile Ala Asp Ala
    50                  55                  60

Met Glu Lys Val Gly Lys Asp Gly Val Ile Thr Val Glu Glu Ala Lys
65                  70                  75                  80

Gly Ile Glu Asp Glu Leu Asp Val Val Glu Gly Met Gln Phe Asp Arg
                85                  90                  95

Gly Tyr Leu Ser
            100

<210> SEQ ID NO 13
<211> LENGTH: 31
<212> TYPE: PRT
<213> ORGANISM: Helicobacter pylori

<400> SEQUENCE: 13

Lys Asp Gly Val Ile Thr Val Glu Glu Ala Lys Gly Ile Glu Asp Glu
1               5                   10                  15

Leu Asp Val Val Glu Gly Met Gln Phe Asp Arg Gly Tyr Leu Ser
            20                  25                  30
```